United States Patent
Gutierrez

(10) Patent No.: US 7,122,337 B2
(45) Date of Patent: *Oct. 17, 2006

(54) **METHOD FOR DETERMINING CALCIOTROPIC ACTIVITY OF A PREPARATION OF *PADINA PAVONIC* ALGAE**

(75) Inventor: Gilles Gutierrez, Lyons (FR)

(73) Assignees: Texinfine SA, (FR); Patrinove SC, (FR)

( * ) Notice: Subject to any disclaimer, the term of this patent is extended or adjusted under 35 U.S.C. 154(b) by 209 days.

This patent is subject to a terminal disclaimer.

(21) Appl. No.: 10/804,748

(22) Filed: Mar. 19, 2004

(65) Prior Publication Data

US 2004/0223978 A1    Nov. 11, 2004

Related U.S. Application Data

(62) Division of application No. 09/947,898, filed on Sep. 6, 2001, now Pat. No. 6,811,999.

(51) Int. Cl.
| | | |
|---|---|---|
| *C12N 1/00* | (2006.01) | |
| *C12N 1/12* | (2006.01) | |
| *C12P 1/00* | (2006.01) | |
| *C12Q 1/00* | (2006.01) | |
| *C12Q 1/02* | (2006.01) | |

(52) U.S. Cl. .............. 435/29; 424/400; 435/4; 435/41; 435/243; 435/257.1; 435/946

(58) Field of Classification Search ............... None
See application file for complete search history.

(56) References Cited

FOREIGN PATENT DOCUMENTS

JP    2001-139419    *    5/2001

* cited by examiner

*Primary Examiner*—David M. Naff
*Assistant Examiner*—Deborah K. Ware
(74) *Attorney, Agent, or Firm*—Charles A. Muserlian

(57) ABSTRACT

A method of determining calciotropic activity of a preparation of algae of the genus *Padina pavonica*. The algae preparation may be in the form of a powder or an extract. The method consists of culturing human or animal osteoblasts in a culture medium containing calcium ions in a well plate. The preparation is added thereto and non-fixed calcium ions are eliminated in the culture medium. Further, the culture medium is acidified to destroy an extracellular matrix formed by the osteoblasts in the culture medium. Thereafter, filtering of the culture medium is carried out and then a concentration of fixed calcium ions in the osteoblasts is determined and compared with a calibration scale of a known activator of the fixation of calcium or in the presence of an inhibitor of the fixation of calcium or both.

10 Claims, 2 Drawing Sheets

METHOD FOR DETERMINING CALCIOTROPIC ACTIVITY OF A PREPARATION OF *PADINA PAVONIC* ALGAE

PRIOR APPLICATION

This application is a division of U.S. patent application Ser. No. 09/947,898 filed Sep. 6, 2001, now U.S. Pat. No. 6,811,999.

BRIEF SUMMARY OF THE INVENTION

The present invention relates to the field of chemistry and more particularly to that of plant chemistry.

More especially, it has as its aim a new process for obtaining a titrated preparation based on algae with active principles ensuring the fixing of calcium by the osseous cells.

Its specific aim is a process for obtaining powders or extracts from the alga *Padina pavonica*, titrated with active principles by means of a coefficient of equivalence with estradiol, which consists of dosing the extract or the powder of *Padina pavonica* using a method in which osteoblasts are cultivated in a medium rich in calcium ions, an analysis is made of the calcium fixed by the cells of the extracellular matrix in the presence or absence of agents antagonistic to the fixing of calcium, and the results are expressed either in arbitrary or international units in relation to a reference standard or by reference to the known activity of fixed doses of estradiol or of any other agent favouring the fixing of calcium.

DETAILED DESCRIPTION OF THE INVENTION

More precisely, the process according to the invention consists of preparing a suspension of a human or animal osseous cell line, by adjusting the cellular density determined by turbidimetry or by calculating from a reference value, leaving to incubate for one to three days at 37° C. in the presence of carbon dioxide and of a complete culture medium (CCM), adding to some wells an agent inhibiting the fixing of calcium or a calciotropic hormone, and some extract to be titrated, eliminating the supernatants from the culture, rinsing out the wells with a rinsing medium without calcium or magnesium (P.B.S. for example) in such a way as to eliminate the non-fixed calcium from the culture medium, eliminating the supernatant fractions, and adjusting the volume of the dispersion with a fixed volume of mineral acid such as hydrochloric acid, sulphuric acid, phosphoric acid or perchloric acid or with any other product capable of destroying the extracellular matrix built up by the cells being cultured. In conclusion, the mixture is adjusted and the calcium is dosed, for example according to the standard AFNOR no. NT-690.005.

The dosage of the calcium constitutes an indicator of activity which is easy to determine. The fixing of the calcium by osteoblasts or cells from a cell line is dependent on the calciotropic agents activating the fixing of calcium (estradiol, vitamins D3, calcitonin) or agents deleterious to the fixing of calcium such as inhibitors of the calcic canals (verapamil, cinchonine or diltiazem), or pro-inflammatory cytokines: prostaglandins, interleukins, PAF etc.

The extracts or powders of the algae *Padina pavonica* have the effect of stimulating biological activity (synthesis of proteins and glycoaminoglycanes) but also act to restore physiological functions such as the fixing of calcium by osteogenic cells. For this, the fixed calcium is dosed with a fixed cell line, such as for example the cell line UMR 106 or the line G 292, in the presence or not of deleterious agents such as inhibitors of the calcic canals and pro-inflammatory agents such as IL 1. Normal osteoblasts give good results, but their availability presents a problem. The preparation to be analysed is tested in parallel on the same cell line, in the presence or not of these same deleterious agents. The quantity of fixed calcium in relation to that obtained with the calciotropic agent and with those obtained in the presence of agents inhibiting the fixing of calcium are compared.

In fact, it has been found that the active molecules of the alga *Padina pavonica* (MAPP) kept their property of improving the fixing of calcium by the osseous cells, even in the presence of an inhibitor of the calcic canals or an inflammatory agent such as interleukin IL-1. This indicates that the extract of *Padina pavonica* possesses one or more active principles whose mode of action is different from that of known substances which are not capable of improving the fixing of calcium in the presence of a calcic inhibitor.

The difficulty of the situation comes from the fact that the activity of the alga varies greatly, depending on the season, the growth and the stage of development of the plant, the depth, the luminosity and the fact that the technician or final consumer wants a product whose activity is constantly. It is necessary therefore to produce an extract in conditions such that it is possible to be free from the variations in active principles in the plant, and the problems arising such as—what should be the activity of the extract and how obtain a product with a titre that is always constant?

The present invention aims to solve the technical problem outlined above.

The harvesting of plants, their treatment and the manufacture of stabilised extract require the dosage of the activity in the substances treated. The gathering-in of the plant should be carried out when the active principle content is at its optimum level, so it is necessary to determine the moment. The preservation of plants before their processing, the extraction of the raw material, the manufacture of the extract make it necessary to have at one's disposal an analytical method making it possible to quantify the activity of the material.

The production of an extract usually calls for chemical dosage of the active molecule. When the activity is brought about by a family of molecules, it becomes difficult or impossible to refer to a chemical dosage. The difficulty of the problem comes from the fact that the molecules can exist in the form of isomers or tautomers, some active and some inactive. If the isomerism is supported by functional groups, it is possible to dose the functional groups and these support the totality and the exclusivity of the activity of the active principles. We can illustrate this by citing the dosage of anthraquinones with senna, alkaloids, etc. In the case of cardiotonic heterosides of digitalis, anomalies of correlation between the chemical analysis and biological activity have been observed many times, as a result of the multiplicity of the active principles with unequal levels of activity.

If the isomerism is supported essentially by structural elements, the analysis will be more delicate and will require the characteristic structural elements to be disclosed by spectrophotometric measurement, or call for characteristic reactions such as coloration of the functions that may be representative of the molecular family being researched. For example, in the case of cis-trans isomerism, the double link should be functionalized by fixing a reactional function. On this function, it will be possible to fix a chromophore group, by a bonding reaction (isothiocyanate of fluorescein, for example). It is also possible to use mass spectometry but it should be remembered that this technique is destructive, and it will not then be possible to re-verify the activity of the fraction isolated.

In the case of numerous substances, it is usual to dose the activity by biological means, for example in the case of penicillin, numerous vitamins such as vitamin A. vitamin E, antibodies, antigens, certain hormones such as insulin, FSH, GSH, cytokins such as interferon, TNF etc. This technique is applied essentially to dosages which would be impossible by chemical means. The case of vitamins A and E provide a good illustration, since they exist in the form of numerous isomers.

The problem becomes even more complex when dealing with substances without a chromophore group that is easily detectable and whose structure is unknown. In this case, the dosage of the biological activity seems to be the sole method or at least the method of choice.

Amongst the methods of dosage of activity, one finds methods which apply to substances modifying a biological activity of procaryotic or eucaryotic cells. The dosage of biological activity poses the problem of the stability of normal cells or cell lines. Furthermore, the signal analysed may vary according to the operational criteria impossible to specify in many cases. At the time of the usage of these methodologies, the authors are confronted with the variability of response of the cells. The response of the strain should therefore be calibrated in relation to a reference system. This system does not give a good response in the case in question, as it so happens that *Padina* is the only known plant capable of inducing a response on the fixing of calcium in the presence of a calcic inhibitor (Inh-Ca) and in the presence of an inflammatory agent such as IL-1. All the other substances tested hitherto cannot restore the fixing of calcium in the presence of a calcic inhibitor (Inh-Ca).

After numerous technical difficulties, the Applicants have managed to produce a dosage method that is efficient and reproducible.

The material to be tested is dosed on a cell culture. An analysis is carried out of the calcium fixed by the osseous cells. To do this, the calcium fixed by an osteoblastic cell line is dosed. In a non-limiting way, UMR 106 and G292, in the presence or not of deleterious agents such as the Inh-Ca and the IL-1 may be cited. The preparation to be analysed will also itself be tested, on the same cell line in the presence or not of agents such as Inh-Ca and IL-1.

In these same conditions, calcium fixed by the same cell line in the presence of estradiol is dosed and a calibration scale is produced, expressed in weight of estradiol This calibration scale ranges from $10^{-3}$ to $10^{-10}$ mol of estradiol or more frequently between $10^{-7}$ and $10^{-9}$ mol of estradiol. In this way, it is possible to establish a correlation between the activity of the extract of *Padina* and an active quantity of estradiol. We should stress that this comparison is made between the activity of estradiol directly on the cell culture with the active extract of *Padina* in the presence of deleterious agents such as an Inh-Ca or IL-1. So it is not a true weight comparison and it is proposed that the result should be expressed in Units of Activity (UA). A unit of activity is defined as the quantity of extract capable of increasing by 50% the quantity of calcium fixed by 400,000 cells cultivated for 48 hours in the presence of 1 ng of interleukin 1 per 1 ml well. The IL-1 can be replaced by another agent inhibiting the fixing of calcium at an equi-active dose.

The extracts of *Padina* have been described, in particular in the European patent application EP 0.655.250. The algae is then depleted after drying, by a hydrocarbonated solvent such as cyclohexane or acetone, the vegetable matter is separated, and the extracted product is filtered then evaporated until dry. A quantity of dry extract weighed precisely is then dissolved in ethanol. Determining its activity is the object of the present invention. In concrete terms, the process according to the invention consists of preparing a suspension of culture of the human cell line G292 (ECAC no. 901-110522), adjusting the cell density to 400,000 cells per ml of complete culture medium (CCM), supplemented by 10% of fetal calf serum. The cell suspension is distributed at the rate of 1 ml per well on plates of 24 wells. It is left to incubate overnight in an atmosphere of $CO_2$ at 37°. The supernatants are separated then dilution is carried out by a new addition of CCM. An aliquot fraction of IL-1 is prepared and 5 µl of interleukin IL1 solution is added, namely 1 ng per well in the wells for the cells which receive only one inhibiting treatment per IL-1.

For each trial of solution to be titrated, 5 µl of solution of *Padina* extract is added. It is then left to incubate for the length of time necessary to carry out the trial, normally between 24 and 72 hours, and preferably 48 hours. Then the supernatants are eliminated and the cellular waste lumps rinsed three times with buffer PBS without calcium and without magnesium, previously heated to a temperature of 37° C., so as to eliminate all the calcium in solution brought about by the culture medium. After the usual purification processes, the solution is mixed with an acid and the calcium is dosed according to the method defined by the standard AFNOR no. NF-T-90.005. The dosages of calcium are only indicators of activity and can be expressed in arbitrary units. They only have absolute value if the values obtained are compared with those originating from untreated cells or undergoing a reference treatment (IL-1, estradiol, calcic inhibitor, for example).

EXAMPLE I

Fixing the Calcium by the Line of Osteoblasts G 292 Compared with Estradiol, Vitamin D3 and Extract of *Padina* (EPP) in the Presence or not of Interleuking 1.

|  | Controls | IL-1 | E2 | E2/IL-1 | EPP | EPP + IL-1 | D3 | D3 + IL-1 |
|---|---|---|---|---|---|---|---|---|
| Osteoblasts | 1,000 | 0,200 | 1,843 | 0,200 | 2,659 | 2,785 | 1,215 | 0,125 |
| G292 | 1,000 | 0,070 | 2,648 | 0,070 | 0,000 | 2,485 | 1,540 | 0,070 |

Figure 1:
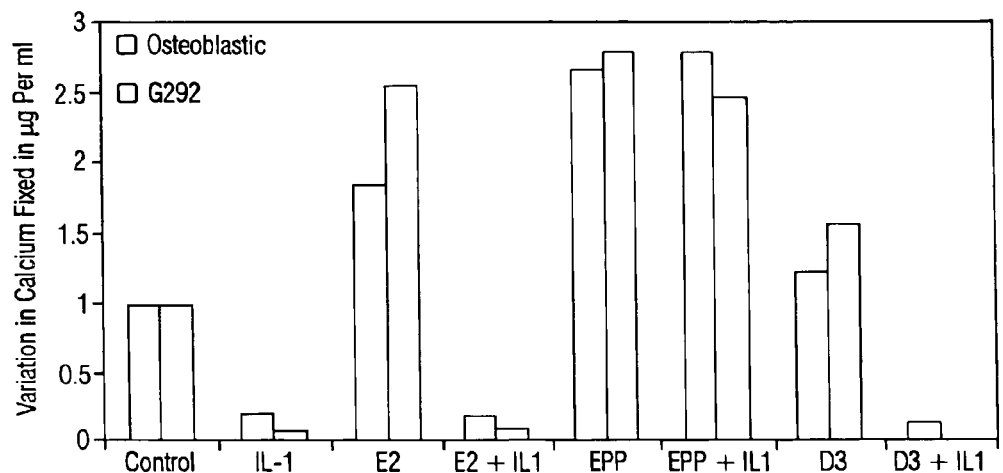
FIG. 1 is a graph of the results of Example 1.

The FIG. 1 schematizes the results obtained under these conditions.

The cells treated solely by interleukin IL-1 have a level of inactivity much lower than that of the control cells. The cells treated by IL-1 and the extract of *Padina* have an activity bordering on that of the control cell.

EXAMPLE II

Calibration of the Extract of *Padina* with Estradiol in the Presence of IL-1

|  | Average | Standard Deviation | 50% |
|---|---|---|---|
| Control | 1.194 | 0.182 | ED = 0.755 |
| IL-1 | 0.315 | 0.002 | ED = Effective dose |
| 100 ng EPP + IL-1 | 0.663 | 0.016 |  |
| 200 ng EPP + IL-1 | 0.671 | 0.129 |  |
| 500 ng EPP + IL-1 | 1.139 | 0.196 |  |
| 1000 ng EPP + IL-1 | 1.153 | 0.216 |  |
| Estr + IL-1 | 0.357 | 0.013 |  |
| Est $10^{-9}$ | 0.706 | 0.102 |  |
| Est $10^{-8}$ Est $10^{-8}$ | 1.115 | 0.167 |  |
| Est $10^{-7}$ | 1.151 | 0.137 |  |

Figure 2:
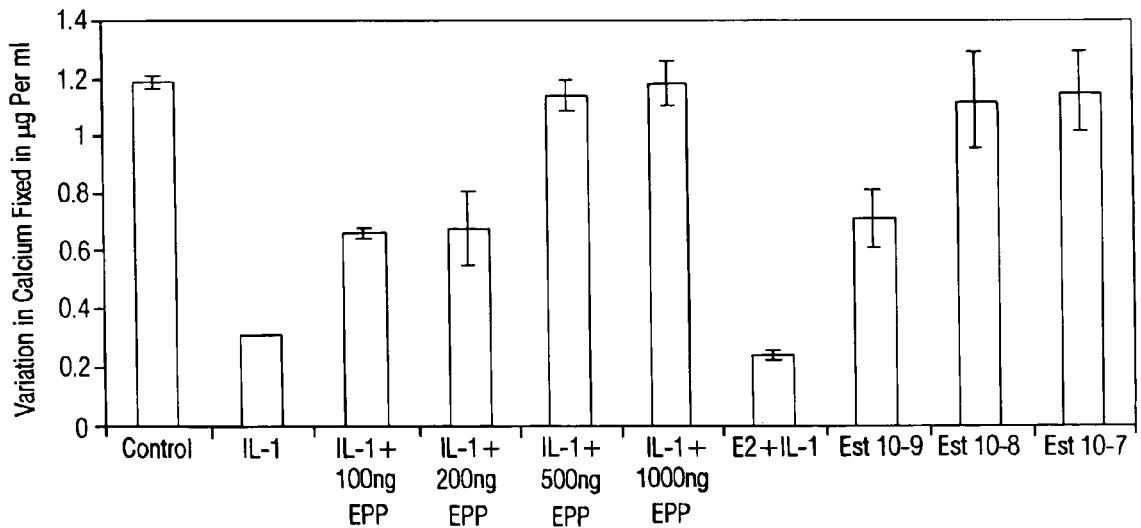
FIG. 2 is a graph of the results of Example 2.

FIG. 2 schematizes the results obtained.

240 ng EPP=$10^{-9}$ M Estradiol=272 µg/L i.e. 272 ng/ml. The dose of 240 ng of extract of *Padina* corresponds with the activity of $10^{-9}$ M estradiol on the fixing of calcium (240 ng of extract of *Padina*=272 µg/l of estradiol, i.e. 272 ng/ml). We may also say that 240 ng of extract have a titre of one unit.

EXAMPLE III

Calibration of the Extract of *Padina* (EPP) and Estradiol on the Fixing of Calcium in Relation to the Effect of a Calcic Inhibitor such as Verapamil.

|  | Average | Standard Deviation | 50% |
|---|---|---|---|
| Control | 1.194 | 0.182 | ED = 0.789 |
| Verap 10 µg | 0.383 | 0.018 | ED = Effective dose |
| 100 ng EPP + Verap. | 0.907 | 0.081 |  |
| 200 ng EPP + Verap. | 1.189 | 0.345 |  |
| 500 ng EPP + Verap. | 1.222 | 0.173 |  |
| 1000 ng EPP + Verap. | 1.249 | 0.140 |  |
| Est + Verap. | 0.373 | 0.023 |  |
| Est $10^{-9}$ | 0.706 | 0.102 |  |
| Est $10^{-8}$ | 1.115 | 0.167 |  |
| Est $10^{-7}$ | 1.151 | 0.137 |  |

Figure 3:
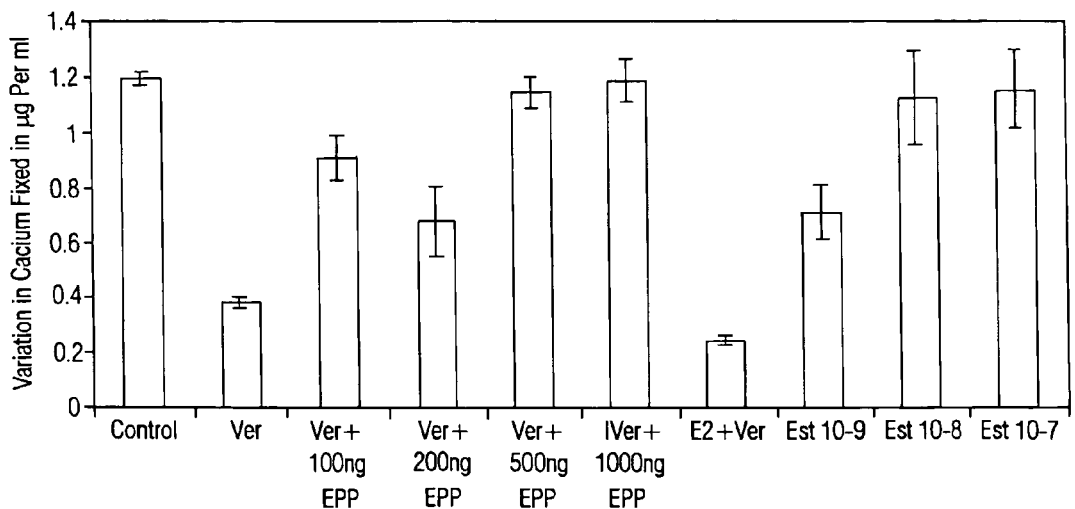
FIGS. 3 and 4 are graphs of the results of Examples 3 and 5, respectively.

The FIG. 3 schematizes the results obtained.
Verap. = Verapamil and Est. = Estradiol

EXAMPLE IV

Variation of the Extract of *Padina* in Relation to Estradiol and a Calcic Inhibitor: Inchonine

|  | Average | Standard Deviation | 50% |
|---|---|---|---|
| Control | 1.194 | 0.182 | ED = 0.627 |
| Cinchonine 10 µg | 0.059 | 0.003 | EPP = Extract |
| 100 ng EPP + Cinchonine | 0.981 | 0.272 | of Padina |
| 200 ng EPP + Cinchonine | 1.163 | 0.147 | Est = Estradiol |
| 500 ng EPP + Cinchonine | 1.100 | 0.246 | ED = Effective |
| 1000 ng EPP + Cinchonine | 1.123 | 0.194 | dose |
| Estr + Cinchonine | 0.357 | 0.013 |  |
| Est $10^{-9}$ | 0.706 | 0.051 |  |

-continued

|  | Average | Standard Deviation | 50% |
|---|---|---|---|
| Est $10^{-8}$ | 1.115 | 0.084 |  |
| Est $10^{-7}$ | 1.151 | 0.068 |  |

EXAMPLE V

Variation of Bone Density of the Lumbar Column in the Course of a Year

| Time | Average time N = 8 | Average variation of patients treated with 200 mg of EPP, N = 8 |
|---|---|---|
| 0 | 0.000 | 0.000 |
| 3 months | −0.230 | 0.515 |
| 6 months | −0.520 | 1.355 |
| 9 months | −0.725 | 1.510 |
| 12 months | −0.845 | 1.725 |

Figure 4:
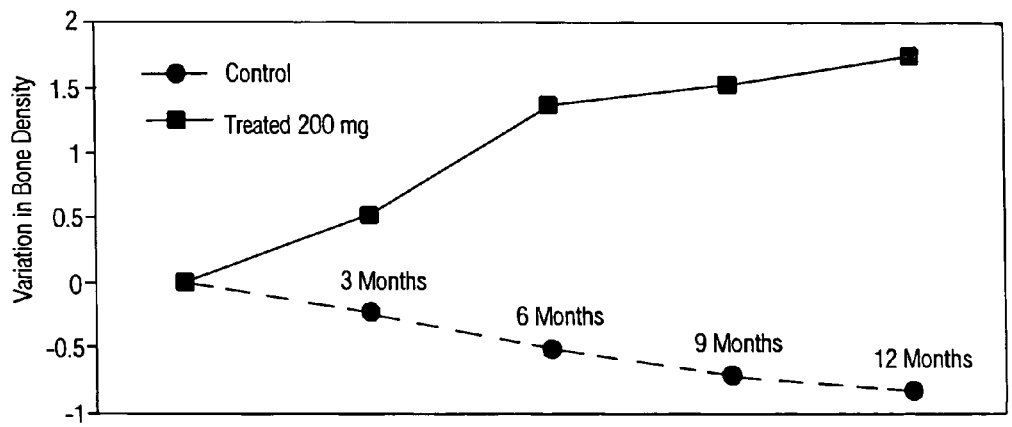

FIG. 4 schematizes the results obtained.

The data on the activity are compared using statistical tests comparing of two averages and two standard deviations (student test). The results are all statistically significant.

Examples 1 to 5 show the agreement of the results obtained by the process according to the invention with the results obtained by biological means and human clinical trials. The few differences discovered (240 ng per 272 ng/ml of estradiol) are principally due to the uncertainty of measures necessary for the evaluation of a biological process.

It may therefore be considered that the biological extracts of *Padina pavonica* have an activity comparable with that of estradiol, but that in no case is it affected adversely by the presence of interleukin or an inhibitor of the calcic canals such as Verapamil or Diltiazem, unlike the calcium fixing agents already known such as estradiol, vitamin D and calcitonine.

The invention claimed is:

1. A method of determining the calciotropic activity of a preparation of algae of the genus *Padina pavonica*, said preparation selected from the group consisting of an extract of said algae and a powder of said algae, said method consisting of culturing human or animal osteoblasts in a culture medium rich in calcium ions in a well plate, adding to said culture medium said extract or a powder of said algae *Padina pavonica* and culturing between 24 to 72 hours, thereafter eliminating non-fixed calcium ions in the culture medium, acidifying the culture medium to destroy extracellular matrix formed by the osteoblasts, thereafter filtering the culture medium to remove solid material, and determining concentration of fixed calcium ions in the osteoblasts in comparison with a calibration scale of a known activator of the fixation of calcium or in the presence of an inhibitor of the fixation of calcium or both.

2. The method of claim 1, wherein results of calculation of calciotropic activity are expressed in comparison with results obtained with a determined amount of an active compound known to promote calcium uptake by the osteoblasts.

3. The method of claim 1, wherein results of calculation of calciotropic activity are expressed comparatively to the known effects of a determined amount of estradiol.

4. The method of claim 1, wherein the osteoblasts are in suspension having a cell density as determined by turbidimetry or by cell density calculation based on a reference value.

5. The method of claim 1, wherein the culturing further comprises adding culture medium and a deleterious agent inhibiting the fixing of calcium to each well of said well plate, thereafter a set volume of dispersion of said extract or powder of algae to be tested is added to the medium in said well plate, and the medium is incubated at 37° C. in an atmosphere of carbon dioxide for one to three days.

6. The method of claim 1, wherein estradiol is used as the known activator of the fixation of calcium.

7. The method of claim 1, wherein the inhibitor of the fixing of the calcium is a pro-inflammatory agent.

8. The method of claim 7, wherein the pro-inflammatory agent is interleukin IL-1.

9. The method of claim 1, wherein the inhibitor of the fixing of the calcium is an agent which blocks the calcium channels.

10. The method of claim 1, in which the inhibitor of the fixing of the calcium is an agent which blocks the calcium channels selected from the group consisting of Verapamil and Cinchonine.

* * * * *